United States Patent
Pfaff et al.

(10) Patent No.: US 6,607,560 B1
(45) Date of Patent: Aug. 19, 2003

(54) PRESS FIT CONNECTION BETWEEN PROSTHETIC COMPONENTS OF JOINT PROSTHESES

(75) Inventors: Hans-Georg Pfaff, Ostfildern (DE); Robert Rack, Plochingen (DE); Paul Silberer, Waghäusel (DE); Wilfried Von Chamier, Stuttgart (DE)

(73) Assignee: Ceramtec AG Innovative Ceramic Engineering, Plochingen (DE)

( * ) Notice: Subject to any disclaimer, the term of this patent is extended or adjusted under 35 U.S.C. 154(b) by 0 days.

(21) Appl. No.: 09/890,700

(22) PCT Filed: Feb. 13, 2000

(86) PCT No.: PCT/EP00/00186

§ 371 (c)(1),
(2), (4) Date: Jan. 14, 2002

(87) PCT Pub. No.: WO00/45748

PCT Pub. Date: Aug. 10, 2000

(30) Foreign Application Priority Data

Feb. 4, 1999 (DE) .......................... 199 04 437

(51) Int. Cl.⁷ .................................................. A61F 2/38
(52) U.S. Cl. .................................................. 623/22.45
(58) Field of Search .......................... 623/22.42, 22.43, 623/22.44, 22.45

(56) References Cited

U.S. PATENT DOCUMENTS

| | | | | |
|---|---|---|---|---|
| 4,921,500 A | * | 5/1990 | Averill et al. ............ | 623/22.45 |
| 5,015,257 A | * | 5/1991 | Crowninshield et al. . | 623/22.45 |
| 5,066,304 A | * | 11/1991 | Crowninshield et al. . | 623/22.45 |
| 5,156,624 A | * | 10/1992 | Barnes ..................... | 623/22.45 |
| 5,362,311 A | * | 11/1994 | Amino et al. ............ | 623/22.45 |
| 5,735,905 A | | 4/1998 | Parr | |
| 5,865,850 A | * | 2/1999 | Matthews ................. | 623/22.43 |

FOREIGN PATENT DOCUMENTS

| | | |
|---|---|---|
| DE | 4008563 | 9/1990 |
| DE | 9109189 | 10/1991 |
| DE | 9103574 | 6/1992 |
| DE | 4441033 | 5/1996 |
| DE | 19517843 | 11/1996 |
| DE | 19640745 | 1/1998 |
| EP | 0038572 | 10/1981 |
| EP | 0457222 | 11/1994 |

* cited by examiner

*Primary Examiner*—David J. Isabella
(74) *Attorney, Agent, or Firm*—Antonelli, Terry, Stout & Kraus, LLP

(57) ABSTRACT

Joint prostheses, in which one joint partner is formed as a socket and the other joint partner is formed as a spherical head which is rotatably mounted in the socket, are known in particular as shoulder-joint and hip-joint prostheses. The force-fit connection, in particular conical jamming, is also used here as the connecting technique between metallic or ceramic spherical heads and the cone. A coupling element (6) is inserted between the cone (5) and the spherical head (3) of the force-fit connection (1). The elasticity and damping properties of the coupling element (6) can be predetermined by its porosity and the structure of its surface.

14 Claims, 3 Drawing Sheets

PRESS FIT CONNECTION BETWEEN PROSTHETIC COMPONENTS OF JOINT PROSTHESES

BACKGROUND OF THE INVENTION

The invention relates to a force-fit connection between prosthesis components of joint prostheses. Components of joint prostheses in accordance with the preamble of the first claim.

Joint prostheses, in which one joint partner is formed as a socket and the other joint partner is formed as a spherical head which is rotatably mounted in the socket, are known in particular as shoulder-joint and hip-joint prostheses. These prostheses, as a rule, are built up in a modular fashion. Hip-joint endoprostheses, for example, consist of the socket, which is inserted into the hip bone, and of the shaft, which is inserted into the femur. The socket consists as a rule of a metallic outer shell into which a shell insert made of ceramic material or a biocompatible plastics material is inserted. A force-fit connection is used here as the connecting technique. A force-fit connection is known, for example, from DE 196 11 248 A1. The shaft has a peg, the so-called cone, onto which the spherical head is slipped. In the case of the modularly constructed endoprostheses, implant components are connected together that are made of different materials and are of different sizes for the purposes of adaptation to the physique of the patient. For example, spherical heads made of a cobalt-chromium alloy or made of an aluminium-oxide ceramic material are slipped onto a cone made of titanium. The force-fit connection, in particular conical jamming, is also used here as the connecting technique between metallic or ceramic spherical heads and the cone. In this connection, the spherical head which has a conical bore is placed upon the cone. After the spherical head has been slipped onto the cone, fixing is effected by hitting the spherical head.

In the case of conical jamming, the joint surfaces of the cone and the bore in the spherical head must be worked in an extremely precise manner, because otherwise the durability of the conical fit is jeopardized as a result of uneven introduction of force into the spherical head or the cone respectively. If the spherical head is made of ceramic material, stress peaks in the material can result in the formation of cracks and, in the worst case, the destruction of the spherical head. In order to make the conical fit more reliable, coupling elements have therefore been proposed and these are to compensate for dimensional inaccuracies and are to improve the durability of the force-connection. Such a coupling element is known from DE 40 08 563 A1. It is a sleeve made of metal, preferably of titanium, which has a predetermined degree of roughness on its inner and outer faces. After the spherical head has been placed on the cone and after the roughness has been lost, such a sleeve is so rigid, like the cone itself, with the disadvantages set forth above.

SUMMARY OF THE INVENTION

The object of the present invention is to propose, for joint prostheses, an improved force-fit connection between the spherical head and the cone.

The object is achieved by using a coupling element for rendering uniform the transfer of force between the cone and the spherical head, the elasticity and damping properties of the coupling element being predetermined by its porosity and the structure of its surface.

As a result of an aimed for configuration of the surface structure and the internal structure of the coupling element, in particular its porosity, in accordance with the invention, its elasticity and damping properties and thus the introduction of force into the bodies that are coupled therewith are predetermined. As a result of the force-fit connection in accordance with the invention having a porous coupling element with a structured surface it is also possible to exchange damaged spherical heads without having to remove the shaft, even if the state of the surface of the cone would no longer permit the spherical heads to be placed directly thereon.

One embodiment of the porous coupling elements can be produced as a wound body. As a result of controlled deposition of the threads on a body, which has at least approximately the shape that the coupling element is to obtain, it is possible to control the porosity of the wound body and its surface structure. In the case of cylindrically or conically shaped wound bodies, which can be wound, for example, on tubes on spooling machines, the porosity can be predetermined by adjusting the intersection angle, the spacing of the threads deposited side by side (thread traverse) and also the thread tension during the winding process.

Instead of having a wound body, the coupling element can also have a structure that is like that of a woven fabric. It is possible to influence the porosity and the nature of the surface, the roughness, by means of the mode of weaving, that is, the distance of the threads from each other and their interlacing. In addition, the structure of a coupling element consisting of a plurality of layers of woven fabric affords the possibility of influencing the porosity and thus its deformability.

The surface structure in the case of the wound bodies and in the case of the woven fabrics is substantially determined by the diameter of the threads, the shape of the threads—flat, round or twisted—and also the deposition or interlacing of the threads. Owing to the fact that, both in the case of the wound body and also in the case of a structure like that of a woven fabric, the threads can be worked with variable spacing from each other, elevations develop at the points of intersection of the threads on the surface of the wound bodies or the woven fabric, whilst the pores develop on account of the intervals between the threads. The points of intersection and the intervals between the threads therefore influence on the surface the structure, the roughness, of the coupling element.

Although the coupling element between the spherical head and the cone is substantially screened from the bone and the body tissue, the possibility of interaction between the material of the coupling element and the body tissue does nevertheless exist, on account of the body fluid. For this reason, the threads of the wound bodies or the woven fabrics are produced from a biocompatible material. All the materials which have already been considered as being biocompatible in prosthetics are suitable as materials. The threads can therefore be made, for example, of metal or a metal alloy, such as, for example, chromium, tungsten- chromium, cobalt-chromium, and titanium. Threads made of carbon that have a particularly high level of tensile strength and, moreover, consist of an element that is present in the body itself have proved to be particularly effective. In particular, by using threads made of carbon it is possible to configure a coupling element in such a way that when loaded it does not deform in the direction of its surface extension.

In order to facilitate the production of a coupling element in the correspondingly desired form, it is advantageous if the threads or the layers of threads are fixed in their position by means of a fixing agent. Epoxy resins can be used, for example, as fixing agents. It is also essential here that the fixing agent be made of a bioinert or biocompatible material.

In a further embodiment, besides wound bodies and woven fabrics, it is also possible to produce coupling elements as sintered bodies or sponge bodies. For example, coupling elements can be sintered in any desired shape from spheres or grains of a biocompatible material, in particular from the known biocompatible metals already listed above, in which case the pore size within the sintered body and also its surface structure are simultaneously determined by the sphere size or grain size. In the case of sponge bodies, which can be produced, for example, by gassing molten metals, it is possible to influence the pore content and the pore size by appropriate supply of the gassing agent.

Depending on the anticipated loading and size of the endoprosthesis, the coupling element for a spherical head can have a wall thickness between 0.3 mm and approximately 2 mm. A range between 0.5 mm and 1 mm is preferred. The wall thickness of the coupling element is taken into consideration when the conical bore is introduced into the spherical head. The proportion of pores of the coupling element, matched to the desired elasticity and damping, can be adjusted to a proportion between 20% and 90%, with a proportion of pores of approximately 40% being regarded as optimum. The higher the proportion of pores is, the more elastically the coupling element behaves.

The roughness of the surface of the coupling element also exerts an influence on the elasticity and damping. With a comparatively high level of surface roughness, the deformability of the surface increases and, as a result, the elasticity of the coupling element and its damping properties increase. The surface roughness is likewise matched to the endoprosthesis and, there can be a roughness-height Ra lying, between 2 $\mu$m and 300 $\mu$m. A roughness-height of approximately Ra=60 $\mu$m has proved to be advantageous.

The surface structure, that is, the roughness-height, as set forth above, is influenced by the winding processes or the weaving processes or by the sintering technique or the pore production. In particular, in the case of the coupling elements that are sintered from metallic materials and in the case of the sponge bodies, it is possible to influence the structure and thus the roughness further in a controlled manner by means of subsequent treatment of the surface, for example by grinding, sand-blasting or over-twisting.

BRIEF DESCRIPTION OF THE DRAWINGS

The invention is explained in greater detail with reference to exemplifying embodiments.

In the drawings.

DETAILED DESCRIPTION OF THE PREFERRED EMBODIMENT

Figure 1:
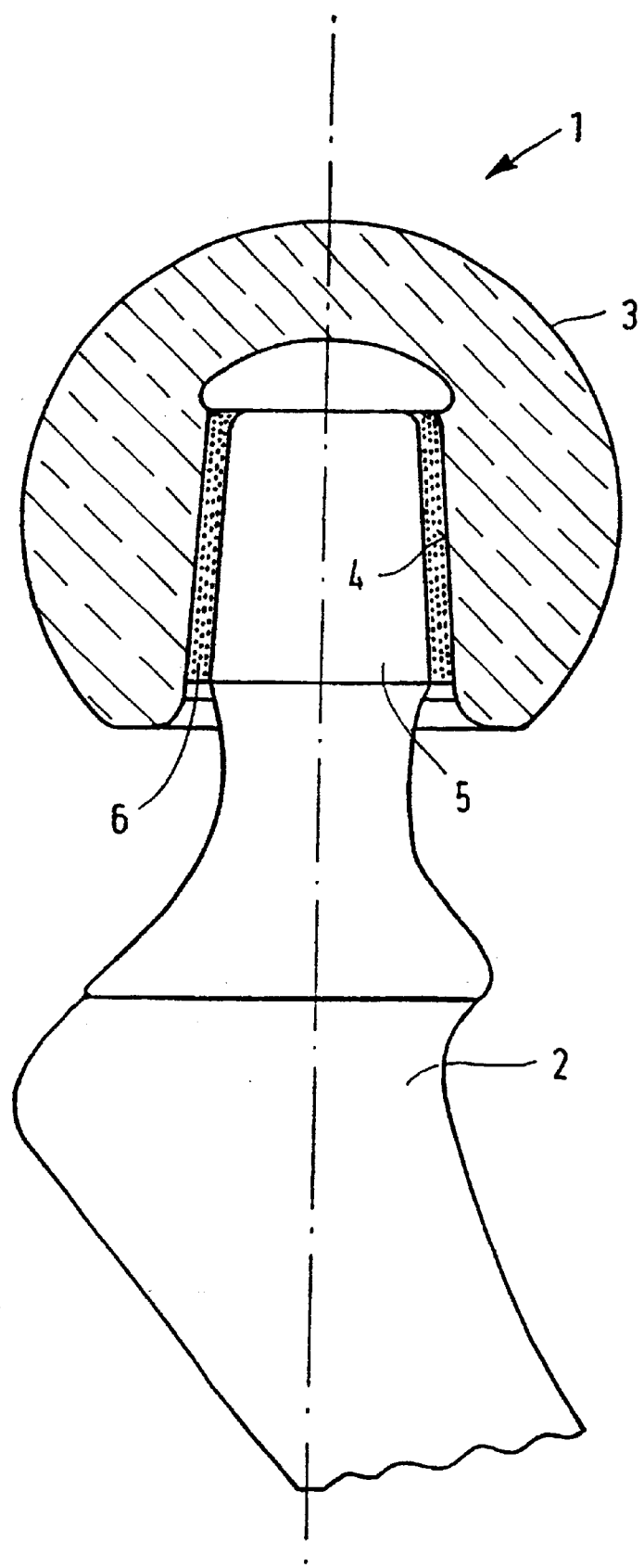
FIG. 1 shows a force-fit connection in accordance with the invention, consisting of a cone and a spherical head made of ceramic material that is shown in section and which is placed on the cone, with a coupling element being arranged between the cone and the spherical head.

In FIG. 1 a force-fit connection in accordance with the invention between a spherical head made of ceramic material and a cone on a shaft of a joint prosthesis is denoted by 1 and is shown on an enlarged scale. A shaft 2 carries a spherical head 3, shown in section, that is made of ceramic material, for example aluminum oxide. The spherical head 3 has a conical bore 4 to receive the cone 5 of the shaft 2. The shaft 2 and its cone 5, in the present exemplifying embodiment, are made of a titanium alloy, for example TiAl6V4. For the purpose of illustration, the coupling element 6 between the conical bore 4 of the spherical head 3, the forcing surface, and the cone 5 is shown to an enlarged scale.

Figure 2:
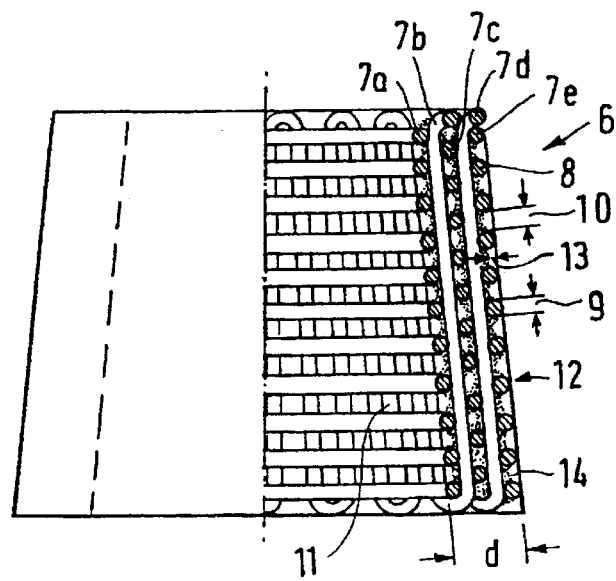
FIG. 2 shows a partial section through a coupling element which is formed from a wound body.

FIG. 2 shows a detail of the coupling element 6 which, in the present exemplifying embodiment, has been formed from a wound body. Five layers of threads 7a to 7e lying one upon the other and producing the wall thickness d of the wound body in the non-deformed state can clearly be seen. The individual threads 8 are deposited side by side. As can be seen from the representation, their diameter 9 and also their spacing 10 from each other determine the dimensions of the pores 11. It can be seen at the same time that the diameter 9 of the threads 8 on the surface 12 substantially determines the roughness 13. Furthermore, the diameter and the depth of the pores 11, which communicate with the surface 12 and as a result, are open, influence the roughness 13 of the surface 12. As can be seen, furthermore, from FIG. 2, the threads are fixed in their position by means of a fixing agent 14, for example by means of an epoxy resin.

Figure 3:
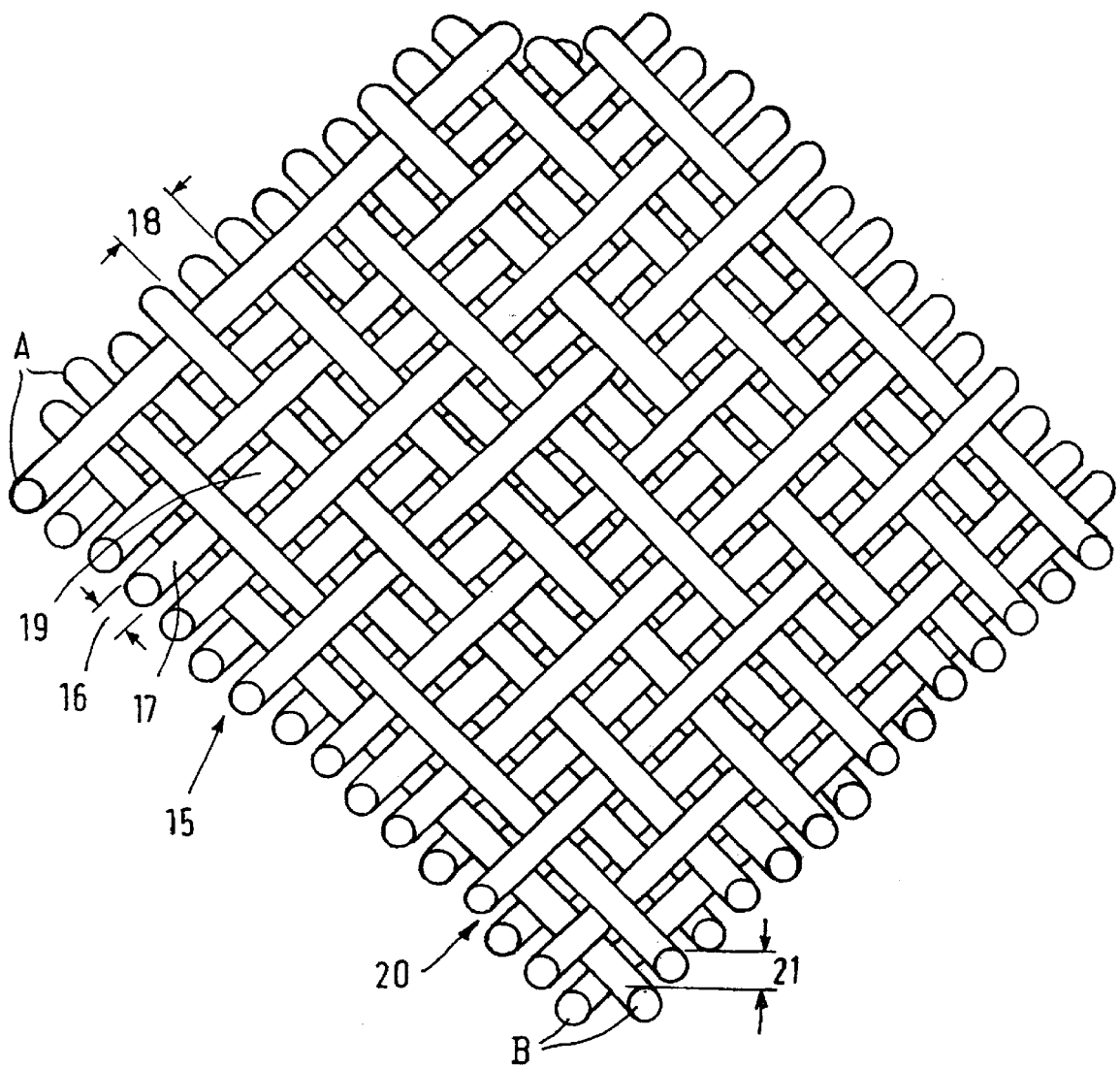
FIG. 3 shows a detail of a coupling element which has a structure like that of a woven fabric.

FIG. 3 shows the structure of a further exemplifying embodiment for a coupling element 15 which is constructed of two layers of woven fabric A and B. Here, as well, it can clearly be seen that the diameter 16 of the threads 17 and also their spacing 18 from each other within the respective layer of woven fabric A or B and also between the individual layers of woven fabric A and B influence the size of the pores 19 and also the structure of the surface 20 and thus the roughness 21.

Figure 4:
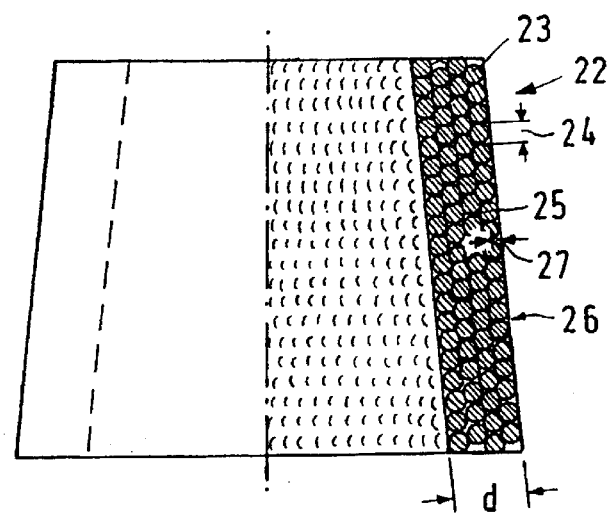
FIG. 4 shows a partial section through a coupling element which is a porous sintered body.

A detail of another exemplifying embodiment of a coupling element 22, which is a sintered body, is shown in FIG. 4. The sintered body 22 has the wall thickness d and consists, in this exemplifying embodiment, of spheres 23 of a biocompatible metal that are sintered together. The diameter 24 of the spheres 23 determines the dimensions of the pores 25 and also the surface structure of the surface 26 and thus its roughness 27.

Figure 5:
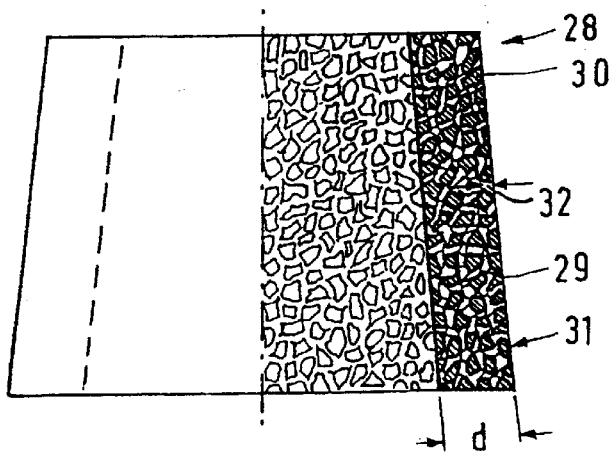
FIG. 5 shows a partial section through a coupling-element which is a sponge body.

FIG. 5 shows a detail of a coupling element 28 which is a sponge body. In this exemplifying embodiment, the structure of the coupling element 28 having the wall thickness d, in contrast to the previous exemplifying embodiment, is determined by the size of the pores 29 which are introduced into the biocompatible metal 30. The pores are formed in an irregular fashion and are partly interconnected and thus form a sponge structure. The pores can be produced in the metal by gassing or by means of so-called space-retainers during the sintering process. Space-retainers are materials that have the shape and size of the pores and which combust without residue during the sintering process. The metal 30 is structured by means of the pores 29. On the surface 31, the roughness 32 is influenced by the dimensions of the pores 29. The smaller the pores 29 are, the less the roughness 32 is.

What is claimed is:

1. A coupling element providing a force fit connection between prosthesis components of a joint prosthesis, in which the one prosthesis component is inserted into bone tissue and bears a cone on which a spherical head is placed that articulates another socket-shaped joint partner, the coupling element being provided between the cone and the spherical head for rendering a transfer of force uniform, the coupling element comprising a porous biocompatible material having a porosity and surface structure defining predetermined elasticity and damping properties.

2. The coupling element according to claim 1, characterised in that the coupling element is a wound body comprising biocompatible threads.

3. The coupling element according to claim 1, characterised in that the coupling element comprises a woven fabric that is produced from biocompatible threads.

4. The coupling element according to claim 2, characterised in that the biocompatible threads are metallic threads.

5. The coupling element according to claim 2, characterised in that the biocompatible threads are made of carbon.

6. The coupling element according to claim 2, characterised in that the biocompatible threads are fixed in position by a fixing agent.

7. The coupling element according to claim 1, characterised in that the coupling element is a porous sintered body that consists of a biocompatible metal or a biocompatible metal alloy.

8. The coupling element according to claim 1, characterised in that the porous biocompatible material is a biocompatible metal or a biocompatible metal alloy having irregularly formed interconnecting pores forming a sponge structure.

9. The coupling element according to claim 1, characterised in that a wall thickness (d) of the coupling element lies between approximately 0.3 mm and 2 mm.

10. The coupling element according to claim 1, characterised in that the pore volume is between 20% and 90%.

11. The coupling element according to claim 10, characterised in that the pore volume is approximately 40%.

12. The coupling element according to claim 1, characterised in that the roughness of the surface of the coupling element has a roughness-height Ra of approximately 2 $\mu$m to 300 $\mu$m.

13. The coupling element according to claim 12, characterised in that the roughness-height Ra is approximately 60 $\mu$m.

14. The coupling element according to claim 1, characterised in that a wall thickness (d) of the coupling element lies between approximately 0.5 mm and 1 mm.

\* \* \* \* \*